(12) United States Patent
Dorn

(10) Patent No.: US 6,334,860 B1
(45) Date of Patent: Jan. 1, 2002

(54) BIPOLAR MEDICAL INSTRUMENT

(75) Inventor: Jürgen Dorn, Neulussheim (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/638,947

(22) Filed: Aug. 16, 2000

Related U.S. Application Data

(63) Continuation of application No. PCT/EP99/08517, filed on Nov. 6, 1999.

(30) Foreign Application Priority Data

Dec. 18, 1998 (DE) .......................................... 198 58 512

(51) Int. Cl.[7] .............................................. A61B 18/18
(52) U.S. Cl. ............................. 606/48; 606/50; 606/51
(58) Field of Search ............................. 606/41, 48, 50, 606/51, 52

(56) References Cited

U.S. PATENT DOCUMENTS

| | | | |
|---|---|---|---|
| 5,151,102 A | | 9/1992 | Kamiyama et al. ........... 606/51 |
| 5,779,701 A | * | 7/1998 | McBrayer et al. ............ 606/50 |
| 5,853,412 A | | 12/1998 | Mayenberger ............... 606/51 |
| 6,001,096 A | * | 12/1999 | Bissinger et al. ............ 606/50 |
| 6,050,996 A | * | 4/2000 | Schmaltz et al. ............. 606/51 |
| 6,086,586 A | * | 7/2000 | Hooven ....................... 606/50 |

FOREIGN PATENT DOCUMENTS

| | | |
|---|---|---|
| DE | 43 12 284 A1 | 11/1993 |
| DE | 44 21 822 C1 | 10/1995 |
| DE | 196 08 716 C1 | 4/1997 |
| DE | 198 58 512 C1 | 5/2000 |
| EP | PCT/EP99/08517 | 11/1999 |
| FR | 90 06806 | 5/1990 |
| US | PCT/US94/09301 | 8/1994 |

* cited by examiner

*Primary Examiner*—Linda C. M. Dvorak
*Assistant Examiner*—David M. Ruddy
(74) *Attorney, Agent, or Firm*—St. Onge Steward Johnston & Reens LLC

(57) ABSTRACT

A bipolar medical instrument is provided comprising a tubular shaft having two jaw parts disposed at the distal end of the shaft. The jaw parts are pivotally connected to one another and each forms an electrode to which a high frequency electric power is applicable. The jaw parts comprise metallic bases, which are pivotally connected to one another. The metallic bases each comprise an insulator element on the sides facing one another. A conductive element forming an electrode is connected to each of the insulator elements. Two insulated electrical lines extend through the tubular shaft to the conductive elements and are electrically connected thereto.

12 Claims, 2 Drawing Sheets

BIPOLAR MEDICAL INSTRUMENT

CROSS REFERENCE TO PENDING APPLICATION

This application is a continuation of pending International Application PCT/EP99/08517 filed Nov. 6, 1999, designating the United States.

BACKGROUND OF THE INVENTION

The invention generally relates to a bipolar medical instrument having two jaw parts disposed at the distal end of a tubular shaft, where the two jaw parts are pivotally joined to one another and wherein each jaw part forms an electrode to which high frequency electrical power can be applied.

The German patent DE 196 08 716 discloses such a bipolar medical instrument. The instrument is employed in minimally invasive surgery on the human or animal body in endoscopic operations.

The two jaw parts at the distal end of the tubular shaft are pivotally joined, so that the two jaw parts are opened and closed through actuation of handling means at the proximal end of the tubular shaft. Body tissue is cut and/or grasped with the jaw parts to separate and remove tissue or to shift or move tissue. The jaw parts are correspondingly formed as cutting tools with cutting edges or as grasping tools where the jaw parts when closed engage one another with blunt surfaces.

At least one of the two jaw parts is pivotally joined to the tubular shaft, while the other jaw part is either pivotally or rigidly secured to the shaft.

It is also foreseen in the instrument mentioned at the outset, that both jaw parts form electrodes, to which high frequency electrical power can be supplied. The two jaw parts are each connected respectively with one pole of a high frequency voltage source. When applying bipolar high frequency power, the two jaw parts when acting as a cutting tool achieve a better cutting effect due to the thermal effects of the high frequency current. On the other hand, when acting as a grasping tool a coagulation of the tissue grasped between the jaw parts is achieved through heat generation.

Since the jaw parts, the pivot joint of the jaw parts and the tubular shaft are normally made of metal and are therefore electrically conductive, the problem arises that electrical insulation between the jaw parts forming electrodes must be provided to avoid a short circuiting of the jaw parts, because different potentials are supplied to the jaw parts. The problem of electrical isolation of the two jaw parts is even greater, the smaller the size of the instrument in the jaw part region and in the region of the pivot. This is especially the case when the diameter of the instrument in the pivot region is 5 mm or less.

In the instrument disclosed in DE 196 08 716, electrical insulation is achieved in that ceramic elements are placed in the pivot joint of the two jaw parts, which is otherwise made of metal. The ceramic elements then also form a part of the pivot joint. This type of insulation of the two jaw parts in the pivot region however has the drawback that the ceramic elements must be strongly reduced in thickness if the instrument is to be miniaturized. The normal high frequency voltage on the jaw parts is in the order of 2.5 kV, which means that when reducing the thickness of the ceramic elements, a voltage spark through the ceramic element can take place. A further drawback of the electrical insulation in the pivot region is that the ceramic elements move with the jaw parts and thus are subject to abrasion due to friction over time.

Another bipolar medical instrument is disclosed in the German patent application DE 43 12 284, wherein the jaw parts are completely made of plastic in which the ends of the electrical lines are embedded. The drawback here is that the jaw parts supplied with high frequency power may not always withstand the high heat generation.

The object of the present invention, therefore, is to provide an improved bipolar medical instrument of the type mentioned at the outset, wherein a reliable electrical insulation with constructively simple means is achieved, especially in a miniaturized configuration of the jaw parts and the pivot joint of the two jaw parts.

SUMMARY OF THE INVENTION

According to the present invention, a bipolar medical instrument is provided, comprising:

a tubular shaft having a distal end;

a first and a second jaw part disposed at said distal end of said shaft, said first and second jaw part being pivotally joined to one another, said first jaw part forming a first electrode and said second jaw part forming a second electrode, to which high frequency electric power can be applied;

a first and a second insulated electrical line extending through said tubular shaft, said first electrical line being conductively connected to said first electrode and said second electrical line being conductively connected to said second electrode, each of said first and second jaw part comprising:

a metallic base, said metallic base of said first jaw part being pivotally joined to said metallic base of said second jaw part;

an insulator element disposed on a side of said metallic base facing the other of said first and second jaw part, respectively; and a conducting element joined to said insulator element, which forms said first and second electrode, respectively, and is not in contact with said metallic base and is conductively connected to one of said first and second electric line, respectively.

Instead of insulating the two jaw parts at the pivot joint as in the prior art, the instrument according to the present invention provides electrical insulation on the jaw parts themselves. However, the jaw parts are not formed completely of an insulating material, for example plastic as in the prior art, but each comprises a metallic base giving the necessary high mechanical stability of the jaw parts, which is advantageous for such instruments. The electrical insulation is accomplished by the insulator elements arranged on the sides of the bases facing one another, so that an electrical isolation is achieved. A conductive element is connected respectively to each insulator element to form the electrodes to which high frequency power can be applied. Electric power supply is provided by insulated electrical lines running through the tubular shaft, which extend to and are connected to the conductive elements. The conductive elements are separated from the metallic bases by the insulator elements, so that the jaw parts which are pivotally journaled at the bases are insulated from one another.

In contrast to the prior art, the pivotal connection of the two jaw parts can be metallic and electrically conductive, where isolation measures in the pivot region requiring more space are avoided. The instrument of the present invention can therefore be greatly reduced in size without loss of stability at the pivot joint, because insulation materials, which do not have the same mechanical stability as metals, are avoided as components of the pivot joint.

In a preferred embodiment, a distal end of each of said first and second electrical line is arranged in and enclosed by said associated insulator element and is electrically connected to a projection of said conductive element projecting into said insulator element.

The advantage is that each electrical line is reliably, mechanically secured within its insulator element and on the other hand the conductive element is mechanically secured to the insulator element by the projection extending into the insulator element.

Preferably, said distal end of each of said first and second electrical line is passed through said insulator element from a proximal end thereof to a distal end thereof and is inserted to a small tube of said conductive element which projects into a distal end of said insulator element.

The complete embedding of the electrical line in the insulator element has the advantage that the electrical line is better secured within the insulator element. The electrical lines can be formed of a thin wire surrounded by an insulating mantle. A further advantage is that the electrical line with its insulating mantle can be inserted into the proximal end of the insulator element, so that a possible contact of the electrical line with the metallic base of the respective jaw part is reliably avoided. The outmost distal end of each electrical line, which is then not insulated, is inserted into the tube of the conductive element projecting into the insulator element. In this manner, a reliable electrical contact of the electrical line with the conductive element is achieved.

In a further preferred embodiment, said insulator element distally extends beyond said metallic base and said conductive element is arranged at least on a distal end of said insulator element and forms a tip.

In this embodiment, the effective electrode surfaces of the two jaw parts are located at their respective distal ends, so that tissue can be treated with high frequency power with the tip. With the insulator element extending beyond the associated metallic base to the distal end, a reliable separation of the conductive elements, i.e. the electrodes and the metallic base is achieved.

In a further preferred embodiment, said tip terminates in a branch in a tweezer-like fashion.

This has the advantage that the tweezer-like branches allow a particularly fine treatment of tissue under the influence of the high frequency energy. The peaked branches cause an increased high frequency power density due to a peak effect, so that a cutting function or a cutting-like property of the instrument is possible without having to provide scissor-like cutting means.

Preferably, said conductive element encloses a distal end of said insulator element in the form of a cap.

The advantage is that the conductive elements provide a protective cover of the distal ends of the insulator elements so that the distal ends, which for example are made of ceramic and are less abrasion resistant, are protected against wear.

In a further preferred embodiment, said conductive element has a plate-like form and extends substantially over the entire surface of said insulator element, i.e. the surface of the jaw part opposing the surface of the other of said jaw parts.

With this feature the effective electrode surface of the two jaw parts is advantageously enlarged, so that large surface areas of tissue grasped between the jaw parts can be treated with high frequency electrical energy, i.e. coagulated.

In a further preferred embodiment, said insulator element extends beyond said metallic base in circumferential direction.

With this feature, a sufficiently large spacing of the two metallic bases is achieved in constructively simple manner also along their longitudinal sides in the region of the conductive elements acting as electrodes. A spark discharge is therefore avoided even at high voltages.

In a further preferred embodiment, said insulator element is seated in said respective metallic base.

The advantage is that the insulator elements are securely retained in the metallic bases even at high mechanical loads, which for example can arise when cutting or grasping tissue by closing the jaw part.

In a further preferred embodiment, said insulator element is fixed to said metallic base by means of an adhesive.

A particularly simple and stable connection of the insulator element with the metallic base is achieved, which is also secure against release.

Preferably, said adhesive is heat resistant and/or moisture resistant.

An advantage is that the connection between the insulator element and the metallic base is secure when heat is generated in using the instrument. A further advantage is that the jaw parts can be sterilized in an autoclave at high vapor pressures and high temperatures, so that the present instrument fulfills the strict requirements with respect to sterilization.

In a further preferred embodiment, said insulator element is made of a ceramic material, preferably a ceramic material of high hardness and of less brittleness.

The advantage is that the insulator element of each jaw part possesses high mechanical stability. As the insulator elements are disposed in the working area of the jaw parts and thus make up part of the grasping or cutting tool, a high stability of the jaw parts is achieved, even with high force exertion.

Further advantages can be taken from the following description in connection with the appended drawings. It will be understood that the above-mentioned features and those to be discussed below are not only applicable in the given combinations, but may also be employed in other combinations or taken alone without departing from the scope of the present invention.

An embodiment of the present invention is illustrated in the drawings and will be discussed in more detail below.

DETAILED DESCRIPTION OF A PREFERRED EMBODIMENT

Figure 1:
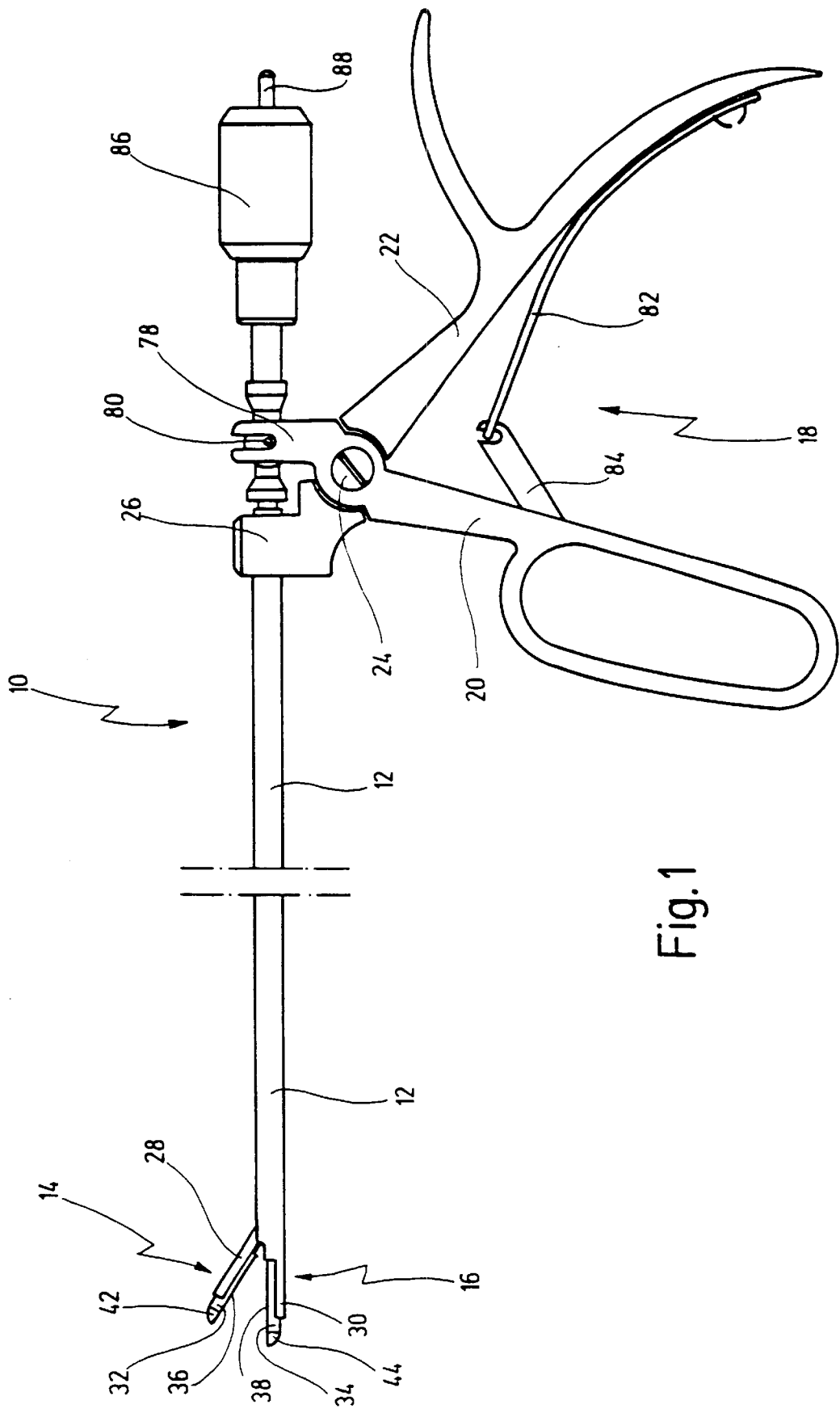
FIG. 1 shows an overall view of a bipolar medical instrument.
Figure 2:
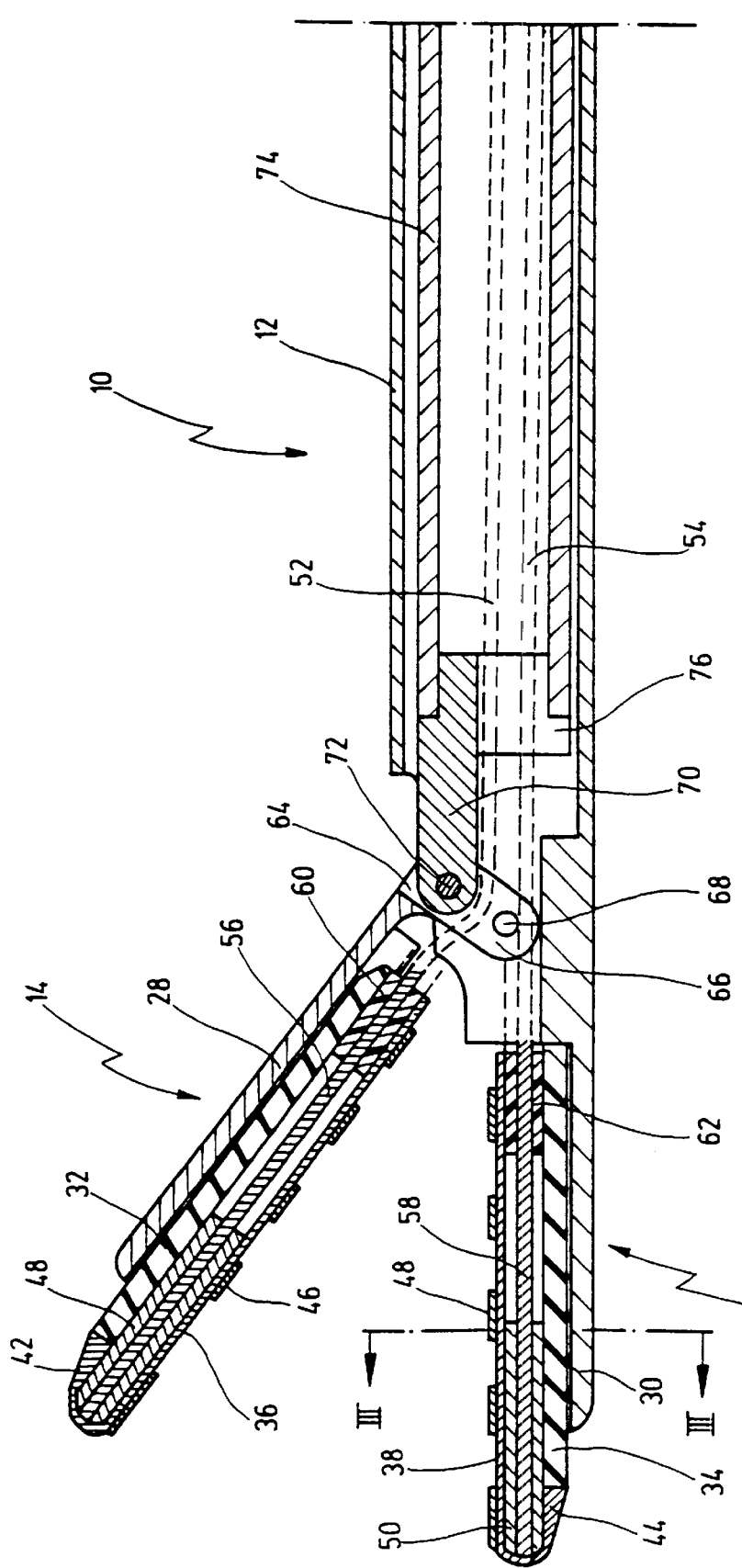
FIG. 2 shows a longitudinal cross section with enlarged scale through the distal end of the instrument in FIG. 1.
Figure 3:
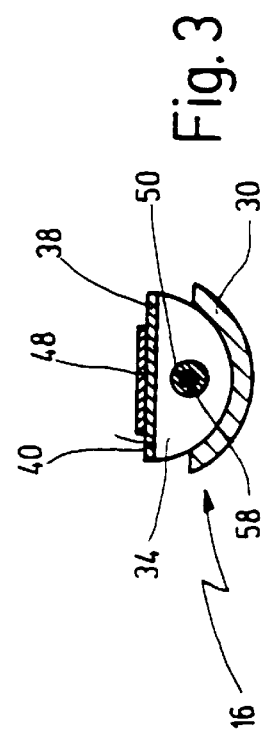
FIG. 3 shows a cross section along the line III—III in FIG. 2 through one of the jaw parts of the instrument.

A bipolar medical instrument is illustrated in FIGS. 1 to 3, which is generally indicated with the numeral 10. The instrument 10 is used for minimally invasive surgery for treating tissue of the human or animal body. The instrument 10 according to this embodiment is used as a grasping instrument for grasping human or animal tissue under control of an endoscope.

The instrument 10 can be especially employed to coagulate the grasped tissue under the influence of high frequency electrical power.

The instrument 10 comprises an extended tubular shaft 12 at whose distal end at first jaw part 14 and a second jaw part 16 is arranged. The jaw parts 14, 16 are pivotally connected to one another as will be discussed below. The first jaw part 14 is moveable, while the second jaw part 16 is rigidly fixed to the shaft 12. In the scope of the present invention however, a configuration is possible where both the jaw part 14 and the jaw part 16 are moveable.

Handling means 18 of the instrument 10 are provided at the proximal end of the shaft 12, which include a first gripping element 20 and a second gripping element 22. The first gripping element 20 is connected with the second gripping element 22 via a joint 24, so that the gripping elements 20, 22 are moveable relative to one another. The first gripping element 20 is moveable relative to the tubular shaft 12, while the second gripping element 22 comprises an extended segment 26 rigidly connected to the shaft 12.

The first jaw part 14 as well as the second jaw part 16 each comprise a metallic base 28, 30. The metal base 30 of the second jaw part 16 is integrally connected as one piece with the shaft 12, while the metallic base 28 is moveable relative thereto.

On the sides facing one another, the metallic bases 28, 30 each have an insulator element 32, 34. The insulator elements 32, 34 are made of a ceramic material having a high hardness and low brittleness. As seen in FIG. 3 showing a cross section through the jaw part 16, the insulator element 34 is seated in the metallic base 30. The metallic base 30 has a rounded, concave form for receiving the insulator element 32 in formfit manner. The metallic base 28 has the same configuration to which the insulator element 32 of the first jaw part 14 is connected.

The insulator elements 32, 34 are connected with an adhesive to their associated metal bases 28, 30. An adhesive is employed which is heat resistant and/or moisture resistant.

A conductive element 36, 38 forming an electrode is connected respectively to each of the insulator elements 32, 34. The conductive elements 36, 38 are made of metal and are therefore electrically conductive. They are arranged on the insulator elements 32, 34 so as not to contact the respective metal bases 28, 30, but to be spaced therefrom at all sides.

The conductive elements 36, 38 have a plate-like form, which extends over the entire width (see FIG. 3) and the entire length (see FIG. 2) of the opposing surfaces of the insulator elements 32, 34. As can be taken from FIG. 3, this surface of the insulator element 32, 34 is flat, as is also illustrated in FIG. 3 with the reference numeral 40.

As shown further in FIG. 2, the insulator element 32 as well as the insulator element 34 extend beyond their associated bases 28 and 30 toward the distal end. The respective conductive elements 36, 38 are also arranged on the respective distal ends of the insulator elements 32, 34. The conductive elements 36, 38 form a tip 42 or 44 at this end. The metallic and electrically conductive tips 42, 44 are connected in one piece with the remaining plate-like section of the conductive elements 36, 38.

The tips 42, 44 surround the distal ends of the respective insulator elements 32, 34 on all sides to form a cap and thus provide protection against wear of the distal ends of the insulator elements 32, 34. The tips 42, 44 can also be more pronounced and the distal ends of the insulator elements 32, 34 can project further than is shown in FIG. 2. The tips 42, 44 can also be configured in the distal direction so that they form tweezer-like branches, which enable a fine treatment of the tissue. With this configuration, a high frequency power density results, so that a cutting function or a cutting-like behavior of the instrument is possible without the presence of scissor-like cutting means.

On their opposing surfaces, the conductive elements 36, 38 also comprise a profile for improved grasping in the form of raised sections 46, 48, where the sections 46 are axially displaced with respect to the sections 48. The raised sections 46, 48 in this embodiment are flat, however, one can consider a grasping profile in the form of a toothed configuration of the conductive elements 36, 38. The raised sections 46, 48 are also metallic and can be formed in one piece with the conductive elements 36, 38 or be soldered thereon. If the conductive elements 36, 38 are formed in a toothed structure, the surface 40 of the insulator element 34 and also the corresponding surface of the insulator element 32 can have a toothed shape to be able to join the conductive elements 36, 38 in form-fit manner with the insulator elements 32, 34.

A projection in the form of a small tube 48, 50 is electrically connected with the tip 42 of the conductive element 36 and respectively with the tip 44 of the conductive element 38. The small tubes 48, 50 are introduced into the associated insulator elements 32, 34 (see FIG. 3) in a bore provided for this purpose.

To apply high frequency electric power to the conductive elements 36, 38 acting as electrodes, two insulated electrical lines 52, 54 are provided, which extend through the tubular shaft 12. A distal end of the line 52 is electrically connected to the conductive element 36 and a distal end of the line 50 with the conductive element 38. The electrical lines 52, 54 are formed as thin, flexible wires surrounded by an insulating mantle.

The distal end 56 of the line 52 as well as the distal end 58 of the line 54 is embedded with all sides closed in the respective insulator elements 32, 34. A corresponding axial bore is made through the insulator elements 32, 34 for this purpose. A portion 60, 62 of the insulating mantle of the electrical lines 52, 54 is introduced into the proximal end of the insulator element 32 and the respective proximal end of the insulator element 34. The distal ends 56, 58 extend to the distal ends of insulator elements 32, 34 and are inserted into the small tubes 48, 50, which are in electrical contact with the conductive elements 36, 38.

As is also seen in FIG. 3, the insulator elements 32, 34 extend beyond the respective associated metal bases 28, 30 also in the circumferential direction, so that a sufficient spacing is maintained between the conductive elements 36, 38 and the metal bases 28, 30.

The pivotal joint of the jaw parts 14, 16 as well as the actuation mechanism for opening and closing the jaw parts 14, 16 will be discussed in detail below. The metallic base 28 of the moveable jaw part 14 comprises at its proximal end a metal forked section 64 formed in one-piece with the rest of the base 28. The right leg portion 66 of the forked section is shown in FIG. 2. The leg 66 is pivotally connected to the tubular shaft 12 with a pin 68, whose inner end is aligned flush with the leg portion 66. The leg portion lying opposite the leg portion 66 (not shown) is also connected with a corresponding link pin with the opposite side of the tubular shaft 12. The link pin 68 as well as the link pin on the other side (not shown) are also made of metal.

The electrical lines 52, 54 are passed through a forked section 64 of the metal base 28 of the jaw part 14. With the forked configuration of the metal base 28, sufficient space is available for passing the lines 52, 54. The forked section 64 engages an arm 70, which is pivotally connected to the leg portion 66 and the leg portion on the opposite side via a further pin 72. The arm 70 as well as the link pin 72 are also made of metal.

The arm 70 at its proximal end is connected to a distal end of a push and pull tube 70 arranged within the tubular shaft 12.

The arm 70 includes a boss 76 at its proximal end for reliable securement with the push and pull tube 74. The push and pull tube is mounted to be axially shiftable within the shaft 12 and extends to the proximal end of the shaft 12 where it is connected to the moveable gripping portion 20 of the handling means 18. The push and pull tube acts as a force transmission element from the moveable gripping portion 20 to the jaw part 14 to open or close the same. The moveable gripping element 20 has a leg portion 78 for this purpose, which is also forked. A pin 80 engages in the cradle of the fork, which in turn is mechanically connected to the push and pull tube 74.

By pressing the gripping elements 20, 22 together, the push and pull tube 74 is urged to the distal direction, where the first jaw part 14 is rotated about the link pin 68 out of the illustrated open position and toward the second jaw part 16 and vice versa. The first gripping element 20 and the second gripping element 22 are biased toward their open position with the jaw part 14 being open by means of a leaf spring 82 and a pivot arm 84.

Finally, a connector housing 86 with a contact pin 88 is arranged at the proximal end of the tubular shaft 12, to which the electrical lines 52, 54 are connected. A high frequency connector (not shown) from a high frequency voltage source (not shown) can be connected to the connector housing 86. The line 52 is then connected to one pole of the high frequency voltage source and the line 54 is connected to another pole of the high frequency voltage source, so that the conductive elements 36, 38 can be charged with a high frequency voltage of varying potential.

It results from the above description that the entire instrument 10 can be made of metal, apart from the insulator elements 32, 34 and the connector housing. In particular, the pivotal connection of the first jaw part 14 with the second jaw part 16, which is formed by the forked sections 64 of the metal base 28, the link pin 68, the arm 70 and the link pin 72, has no insulating materials. Rather, the pivotal joint consists completely of metallic elements, so that a high stability is achieved.

What is claimed is:

1. A bipolar medical Instrument, comprising:
   a tubular shaft having a distal end;
   a first and a second jaw part disposed at said distal end of said shaft, said first and second jaw part being pivotally joined to one another, said first jaw part forming a second electrode, to which high frequency electric power can be applied;
   a first and a second insulated electrical line extending through said tubular shaft, said first electrical line being conductively connected to said first electrode and said second electrical line being conductively connected to said second electrode, each of said first and second jaw part comprising:
   a metallic base, said metallic base of said first jaw part being pivotally joined to said metallic base of said second jaw part;
   an insulator element disposed on a side of said metallic base facing the other of said first and second jaw part, respectively; and
   a conducting element joined to said insulator element, which forms said first and second electrode, respectively, and is not in contact with said metallic base and is conductively connected to one of said first and second electric line, respectively; and
   wherein said insulator element distally extends beyond said associated metallic base and said conducting element is arranged at least on a distal end of said insulator element and has a tip, and wherein said conducting element encloses a distal end of said insulator element in the form of a cap.

2. The instrument of claim 1, wherein a distal end of each of said first and second electrical line is arranged in and enclosed by said associated insulator element and is electrically connected to a projection of said conductive element extending into said insulator element.

3. The instrument of claim 2, wherein said distal end of each of said first and second electrical line is passed through said insulator element from a proximal end thereof to a distal end thereof and is inserted into a small tube of said conductive element projecting into a distal end of said insulator element.

4. The instrument of claim 1, wherein said insulator element distally extends beyond said associated metallic base, and said conductive element is arranged at least on a distal end of said insulator element and has a tip.

5. The instrument of claim 4, wherein said tip terminates in a pointed branch toward its distal end in a tweezer-like fashion.

6. The instrument of claim 1, wherein said conductive element has a plate-like form and extends substantially over said entire surface facing said first and second jaw part of said insulator element, respectively.

7. The instrument of claim 1, wherein said insulator element extends beyond said metallic base in circumferential direction.

8. The instrument of claim 1, wherein said insulator element is seated in said metallic base.

9. The instrument of claim 1, wherein said insulator element is fixed to said metallic base by means of an adhesive.

10. The instrument of claim 9, wherein said adhesive is heat resistant and/or moisture resistant.

11. The instrument of claim 1, wherein said insulator element is made of a ceramic material.

12. The instrument of claim 11, wherein said ceramic material is a ceramic material having high hardness and low brittleness.

* * * * *